United States Patent
Zeman (10) Patent No.: US 8,494,616 B2
(45) Date of Patent: *Jul. 23, 2013

(54) METHOD AND APPARATUS FOR PROJECTION OF SUBSURFACE STRUCTURE ONTO AN OBJECT'S SURFACE

(75) Inventor: Herbert D. Zeman, Memphis, TN (US)

(73) Assignee: Christie Medical Holdings, Inc., Cypress, CA (US)

(*) Notice: Subject to any disclaimer, the term of this patent is extended or adjusted under 35 U.S.C. 154(b) by 1078 days.

This patent is subject to a terminal disclaimer.

(21) Appl. No.: 11/683,851

(22) Filed: Mar. 8, 2007

(65) Prior Publication Data

US 2007/0158569 A1    Jul. 12, 2007

Related U.S. Application Data (63) Continuation-in-part of application No. 10/386,249, filed on Mar. 11, 2003, now Pat. No. 7,239,909, which is a continuation-in-part of application No. 09/487,007, filed on Jan. 19, 2000, now Pat. No. 6,556,858.

(51) Int. Cl.
  *A61B 6/00* (2006.01)
  *H04N 9/47* (2006.01)
  *H04N 7/18* (2006.01)
  *H04N 5/225* (2006.01)

(52) U.S. Cl.
  USPC .............. 600/473; 348/77; 348/136; 348/342

(58) Field of Classification Search
  None
  See application file for complete search history.

(56) References Cited

U.S. PATENT DOCUMENTS

| | | | |
|---|---|---|---|
| 4,541,438 A * | 9/1985 | Parker et al. | 424/9.61 |
| 4,591,918 A * | 5/1986 | Hisano | 348/343 |
| 4,817,622 A * | 4/1989 | Pennypacker et al. | 600/473 |
| 5,519,208 A * | 5/1996 | Esparza et al. | 250/226 |
| 5,608,210 A | 3/1997 | Esparza et al. | |
| 5,772,593 A * | 6/1998 | Hakamata | 600/407 |
| 5,787,185 A | 7/1998 | Clayden | |
| 5,969,754 A * | 10/1999 | Zeman | 348/136 |
| 6,178,340 B1 | 1/2001 | Svetliza | |
| 6,438,396 B1 | 8/2002 | Cook et al. | |
| 6,556,858 B1 | 4/2003 | Zeman | |
| 6,600,946 B1 * | 7/2003 | Rice | 600/473 |
| 6,650,916 B2 | 11/2003 | Cook et al. | |
| 6,665,557 B1 * | 12/2003 | Alfano et al. | 600/473 |
| 6,923,762 B1 | 8/2005 | Creaghan, Jr. | |
| 7,046,835 B2 | 5/2006 | Launay et al. | |
| 7,239,909 B2 * | 7/2007 | Zeman | 600/473 |
| 7,579,592 B2 | 8/2009 | Kaushal | |
| 2005/0008210 A1 | 1/2005 | Evron et al. | |
| 2005/0157939 A1 | 7/2005 | Arsenault et al. | |
| 2005/0187478 A1 * | 8/2005 | Beaudry et al. | 600/476 |
| 2005/0249399 A1 | 11/2005 | Tek et al. | |
| 2006/0122515 A1 | 6/2006 | Zeman et al. | |

* cited by examiner

*Primary Examiner* — Long V. Le
*Assistant Examiner* — Angela M Hoffa
(74) *Attorney, Agent, or Firm* — Butler, Snow, O'Mara, Stevens & Cannada PLLC (57) ABSTRACT

An imaging system illuminates an object with infrared light to enhance visibility of buried structure beneath the surface of the object, and projects a visible light image of the buried structure onto the surface of the object. The system may include an illumination source for generating the infrared light. The system further includes a video imaging device for receiving the infrared light reflected from the object and for generating a video image of the buried structure based on the reflected infrared light. The buried structure may be a subcutaneous blood vessel.

6 Claims, 10 Drawing Sheets

METHOD AND APPARATUS FOR PROJECTION OF SUBSURFACE STRUCTURE ONTO AN OBJECT'S SURFACE

CROSS REFERENCE TO RELATED APPLICATIONS

This application is a continuation-in-part, and claims priority benefit, of U.S. patent application Ser. No. 10/386,249 (filed Mar. 11, 2003) entitled Imaging System using Diffuse Infrared Light, which itself was a continuation-in-part, and claims priority benefit, of U.S. patent application Ser. No. 09/487,007 (filed Jan. 19, 2000) entitled Diffuse Infrared Light Imaging System, which issued as U.S. Pat. No. 6,556,858 on Apr. 29, 2003 (hereby specifically incorporated by reference in their entireties).

BACKGROUND OF THE INVENTION

The present invention is generally directed to generation of diffuse infrared light. More particularly, the invention is directed to an apparatus for illuminating an object with diffuse infrared light, producing a video image of buried structure beneath the surface of the object based on reflected infrared light, and then projecting an image of the buried structure onto the surface of the object.

Some medical procedures and treatments require a medical practitioner to locate a blood vessel in a patient's arm or other appendage. This can be a difficult task, especially when the blood vessel is small and/or the vessel is under a significant deposit of subcutaneous fat or other tissue. The performance of previous imaging systems designed to aid in finding such blood vessels has been lacking. Therefore, an apparatus for enhancing the visual contrast between subcutaneous blood vessels and surrounding tissue is needed.

BRIEF SUMMARY OF THE INVENTION

The foregoing and other needs are met by an apparatus for providing diffuse light towards an object, such as a patient, to enhance visibility of subcutaneous blood vessels. In one embodiment, the apparatus includes an illumination source, such as an array of light emitting diodes, a standard microscope illuminator modified to reflect infrared light by the use of an incandescent light bulb with a gold reflector, or any other illumination source capable of emitting light somewhere in the range of 700 to 1100 nanometers. The illumination source is operable to emit infrared light having a wavelength in the range of 700 to 1100 nanometers toward the object. In the preferred version of this embodiment, the wavelength is in the range of 1000 to 1100 nanometers. The apparatus further includes a diffusing structure if the light emitted by the illumination source is not diffuse. A polarizer is included to polarize the light emitted by the illumination source or sources either before or after diffusion. The apparatus includes a video imaging device, such as a charge couple device or an indium-gallium-arsenide focal plane array, for receiving light reflected from the object. The video imaging device operates to provide a video image of the object based on the reflected light. The generated image is then projected onto the skin of the patient in a manner such that the projected image is coaxial with the image recorded by the video imaging device.

In another embodiment, the apparatus includes at least one illumination source, such as an array of light emitting diodes, a standard microscope illuminator modified to reflect infrared light by the use of an incandescent light bulb with a gold reflector, or any other illumination source capable of emitting light somewhere in the range of 700 to 1100 nanometers, hereinafter RANGE A, and somewhere in the range of 1100 to 1700 nanometers, hereinafter RANGE B. Either the light emitted in RANGE A and RANGE B can be emitted by the same illumination source, or one illumination source can emit light in RANGE A and a different illumination source can emit light in RANGE B. The at least one illumination source is operable to emit infrared light having wavelengths in RANGE A and RANGE B toward the object. At least one power source provides power to the at least one illumination source, and the at least one illumination source can emit infrared light when the power source or sources are enabled. The apparatus further includes at least one diffusing structure, such as, for example, one of the diffusing structures disclosed in patent application Ser. Nos. 10/386,249 or 11/173,452, or a ground glass screen diffuser, providing a level of diffusion to the infrared light in both RANGE A and RANGE B emitted from the illumination source as the emitted light passes through the diffusing structure. Either one diffuser can be used to diffuse the light emitted in both RANGE A and RANGE B, or different diffusers can be used to diffuse the light emitted in RANGE A and RANGE B. In addition, multiple diffusers may be used to diffuse the light emitted in one or both wavelength ranges. A polarizer is included to polarize the light emitted by the source or sources either before or after diffusion. The apparatus includes at least one video imaging device, such as a charge couple device or an indium-gallium-arsenide focal plane array, for receiving light reflected from the object. Images are gathered by the video imaging device or devices in both RANGE A and RANGE B. Either one video imaging device may record two images, one in RANGE A and one in RANGE B, or two video imaging devices may each record one image in one of the ranges. The two images from the two ranges are then compared by an image processor by taking either the weighted difference of the two images with the formula $A*I_1 - B*I_2$ where A and B are constants, $I_1$ is the image in RANGE A, and $I_2$ is the image in RANGE B; the ratio of the two images with the formula $I_1/I_2$ where $I_1$ is the image in RANGE A and $I_2$ is the image in RANGE B; or the ratio of the two images after a constant is added to one or both of the images with the formula $(A+I_1)/(B+I_2)$ where A and B are constants which could be zero, $I_1$ is the image in RANGE A and $I_2$ is the image in RANGE B to create a compared image. While there are multiple ways to compare the two images, one way that works is to do the comparison using the software PV-Wave Version 8.51, a product of Visual Numerics, Inc., running on a personal computer. One skilled in the art would readily ascertain that there are multiple software programs available to perform the image processing required, and there are many alternate methods available to perform that comparison. In addition, the comparison could be performed via firmware, hardware, or analog electronics. The compared image is then projected onto the skin of the patient.

Using the invention described herein, subcutaneous blood vessels that are difficult or impossible to see under white light or under non-diffuse infrared light can be easily seen in a video image, where the subcutaneous blood vessels appear as dark lines against a lighter background of surrounding flesh.

Because of the present invention's departure from the prior art by projecting the image of the buried structure back onto the surface of the object (rather than onto a screen or monitor that is remote from the surface of the object), an observer using the present invention is not subject to the substantial parallax errors that otherwise occur with prior art devices if an observer were to view from off-axis. In other words, because the projection is onto the surface of the object with the present invention, rather than onto a screen remote from the surface of the object, the image stays in the same position on the surface of the object as the observer moves off-axis. An important feature of all embodiments is that the image or images of buried structure viewed by the imaging device or devices should be substantially within a first spectrum outside a second spectrum of the image that is projected back onto the surface of the object, thereby causing the imaging device to be blind to the image that is projected back onto the surface of the object. The substantial non-overlap of the spectrum of the viewed image of the buried structure with the spectrum of the projected image of the buried structure effectively decouples the image processing of the buried structure's image from interference by the projected image. Because the projected image is in a second spectrum, such as the visible light spectrum, and the illumination of the object for the imaging device or devices is in a first spectrum, such as the infrared spectrum, a substantial non-overlap of the two spectrums is maintained. In the preferred embodiments of the invention when used in a medical application to observe subcutaneous blood vessels, the first spectrum will preferably be the infrared spectrum. Also, in the preferred embodiments of the invention, the projected image is coaxial with the received images, such that the projected image most accurately overlays the underlying blood vessels or vasculature portrayed in that image.

BRIEF DESCRIPTION OF THE DRAWINGS

Further advantages of the invention will become apparent by reference to the detailed description of preferred embodiments when considered in conjunction with the drawings, which are not to scale, wherein like reference characters designate like or similar elements throughout the several drawings as follows.

DETAILED DESCRIPTION OF THE INVENTION

Skin and some other body tissues scatter significant amounts of incident light in the near-infrared range of about 700 to 1100 nanometers, RANGE A, in the backwards direction towards the light source while blood scatters light in this range mostly in a forward direction away from the light source. Thus, in video images of body tissue taken under infrared illumination, blood vessels appear as dark lines against a lighter background of surrounding flesh. Subcutaneous fat tends to scatter infrared light almost isotropically and therefore scatters significant amounts of that light back towards the light source. Hence, blood vessels that are disposed below significant deposits of such fat can be difficult or impossible to see. The skin will also scatter light in all directions, but not as uniformly as fat. The light scattered back by skin can therefore be easier to subtract from a recorded image when the illuminating light source is diffuse.

The inventor has determined that when an area of body tissue having a significant deposit of subcutaneous fat is imaged in RANGE A under illumination of diffuse infrared light in RANGE A, the distribution of scattered light in the backwards direction towards the light source is more uniform and is easier to subtract from a recorded image to leave an image of the underlying vasculature. Hence, with diffuse illumination, an image can be produced which has adequate contrast between the blood vessels and the surrounding flesh without obscuring the underlying vasculature with a non-uniform scatter distribution from the skin.

The inventor has also determined that deeper veins become invisible in the range of 1100 to 1700 nanometers, RANGE B, while the surface structure of the skin remains visible. Using this information, the imaging system may be improved by recording images in both RANGE A and RANGE B and "comparing" the two images. The two images from the two ranges are "compared" by an image processor by taking either the weighted difference of the two images with the formula $A*I_1 - B*I_2$ where A and B are constants, $I_1$ is the image in RANGE A, and $I_2$ is the image in RANGE B; the ratio of the two images with the formula $I_1/I_2$ where $I_1$ is the image in RANGE A and $I_2$ is the image in RANGE B; or the ratio of the two images after a constant is added to one or both of the images with the formula $(A+I_1)/(B+I_2)$ where A and B are constants which could be zero, $I_1$ is the image in RANGE A and $I_2$ is the image in RANGE B to create a compared image. This comparison leaves primarily only the underlying vascular structure for projection onto the skin. The inventor has found one successful way of comparing the two images to be taking the weighted difference or ratio using the image processing software PV-Wave Version 8.51, a product of Visual Numerics, Inc, or similar image processing software. In addition to image processing software running on a computer, the images can, of course, be compared using instead firmware, hardware, or analog electronics as the image processor. While the two images are best taken simultaneously, this process also works with two images taken in sequence if they are aligned properly.

If image comparison is not performed, an arrangement of equipment as disclosed in U.S. patent application Ser. No. 10/386,246 works for imaging in RANGE A, although the type of camera or other imaging device must accommodate receiving diffuse light and producing an image at the desired wavelength. For images in the range of more than 900 nanometers, an indium-gallium-arsenide focal plane array camera, such as the FLIR Systems Alpha NIR camera, produces a good quality image and may be preferable, in some instances, to the CCD cameral disclosed in that application.

Figure 1:
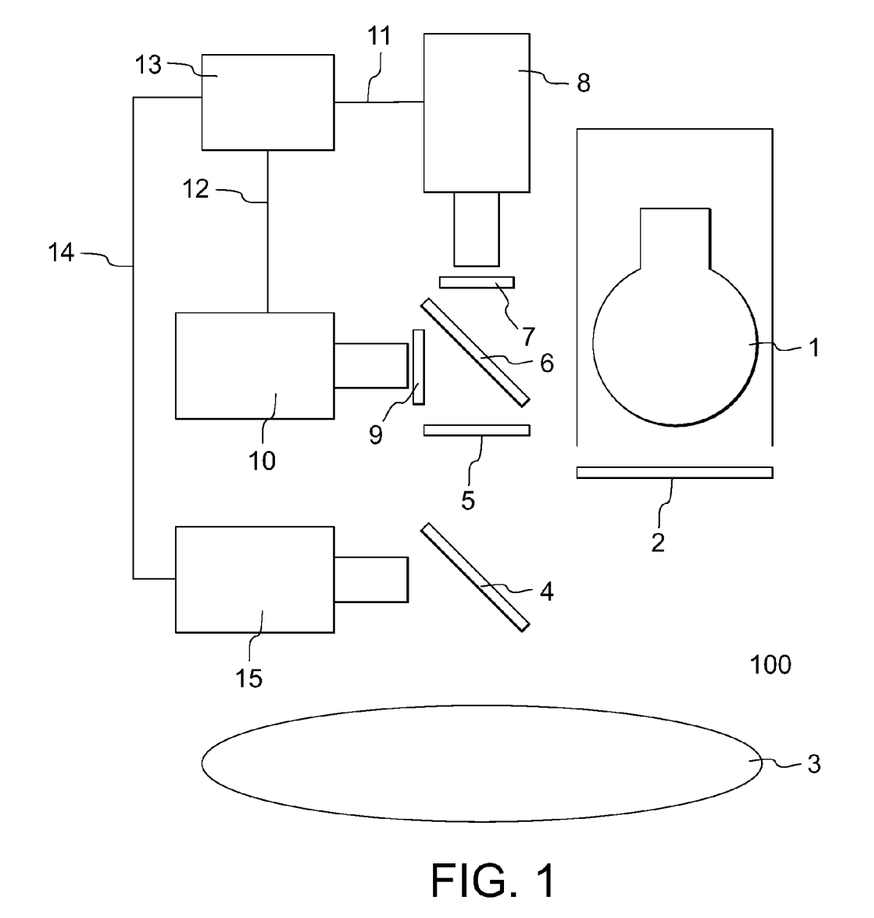
FIG. 1 depicts the apparatus in one possible preferred embodiment of the invention.

Now referring to FIG. 1, FIG. 1 shows one orientation of equipment that works to generate the two images in RANGE A and RANGE B, compare the images to create a compared image, and project the compared image onto the surface of the patient. More specifically, an incandescent lamp or other illumination source which generates light in RANGE A and RANGE B 1 emits light through a first polarizing filter 2 onto the surface of the skin 3 beneath which is the vasculature to be imaged (not shown). The infrared light in RANGES A and B reflected from the skin 3 and underlying vasculature, then pass through cold mirror 4 and a second polarizing filter 5 which is polarized perpendicularly to the first polarizing filter 2 in front of the illumination source 1. The cold mirror 4 transmits infrared light, or at least light in RANGE A and RANGE B, and reflects visible light. A hot mirror 6 directs infrared light in RANGE A to a first imaging device 8 in front of which is a first filter 7 which filters the received light to only receive an appropriate wavelength. A preferred wavelength used in one embodiment of the invention is 1000 nanometers. Thus, in that case the first filter 7 in front of the first imaging device 8 is a 1000 nanometer filter. The hot mirror 6 directs infrared light in RANGE B to a second imaging device 10 in front of which is a second filter 9 which filters the received light to only receive an appropriate wavelength in RANGE B. In one preferred embodiment of the invention, the second filter 9 is a 1200 nanometer filter. The images received by the first imaging device 8 and the second imaging device 10 are transmitted via paths 11 and 12 to an image processor 13 which compares the images to generate a compared image by performing either the weighted difference or ratio of the images and can also perform unsharp masking on the images as unsharp masking is disclosed in U.S. Pat. No. 5,969,754 after comparing the images. The image processor 13 can consist of software running on a computer, firmware, hardware, analog electronics, or any combination thereof. The compared image is transmitted via pathway 14 to a video projector 15 which projects a visible light image of the compared image, detailing the underlying vasculature, created by the image processor onto the surface of the skin 3. The image reaches the skin via the pathway of being generated by the video projector 15, reflecting off of the cold mirror 4 and then reaching the surface of the skin 3. In a preferred embodiment of the invention, the first imaging device 8 may be either a Si CCD camera or an FLIR ALPHA focal plane array camera and the second imaging device 10 is an Indium-Gallium-Arsenide focal plane array camera such as the FLIR ALPHA focal plane array camera. This arrangement also works for performing the imaging of the buried structure without the comparison of two images if the second imaging device 10 is simply not used and the image processor 13 is used solely for applying unsharp masking or other image processing.

Figure 2A:
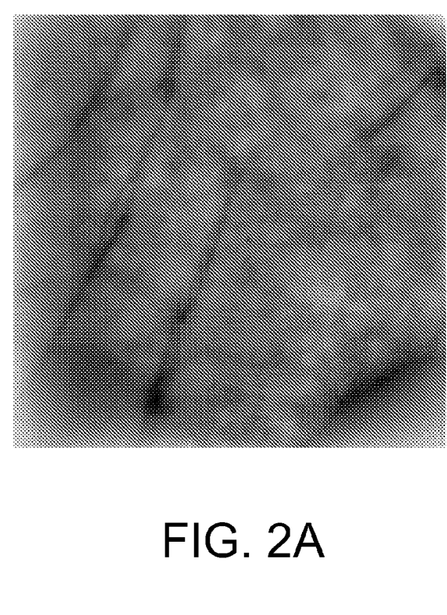
FIG. 2A depicts the image of the left palm of a 62-year-old male, taken at 500-600 nm, circularly polarized.
Figure 2B:
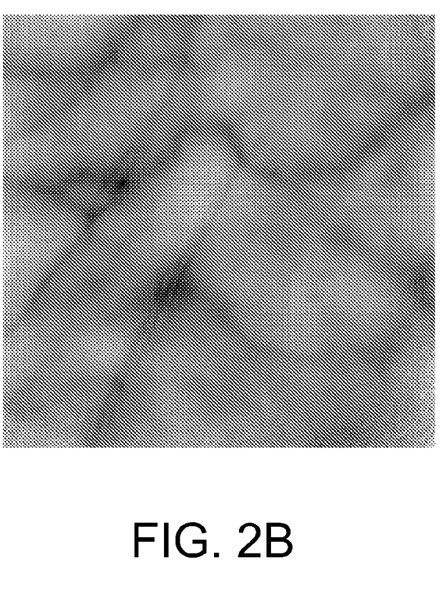
FIG. 2B depicts the image of the left palm of the 62-year-old male of FIG. 2A, taken at 850-900 nm, circularly polarized.
Figure 2C:
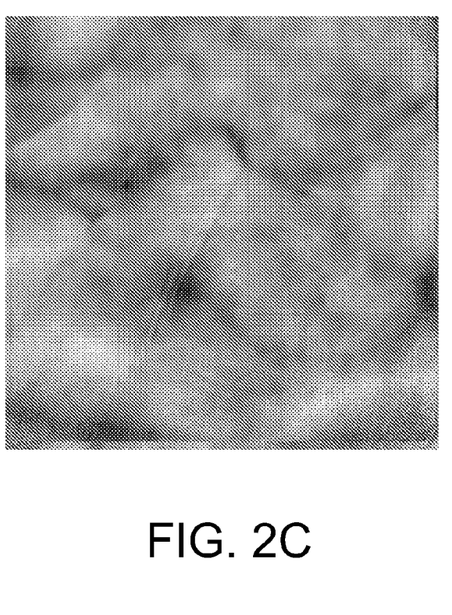
FIG. 2C depicts the weighted difference image between FIG. 2A and FIG. 2B.

FIGS. 2A through 6G show images taken in RANGE A and RANGE B and their weighted difference or ratio. FIGS. 2A through 2C show images of the left palm of a 62 year old male. FIG. 2A is 500-600 nanometers circularly polarized. FIG. 2B is 850-900 nanometers circularly polarized and FIG. 2C is the weighted difference image between FIGS. 2A and 2B. In the green, represented by FIG. 2A, the veins are not visible but the skin creases are clearly visible. In the near infrared, shown in FIG. 2B, both the creases and the veins are visible. In the weighted difference image, FIG. 2C, the creases are significantly suppressed because they are subtracted out with the weighted difference image. However, the skin structure made visible in the green FIG. 2A, shows up in the difference image FIG. 2C making it slightly less clearer than the original infrared image. This is why, in the preferred embodiment of the invention, the image to be subtracted which shows creases to be subtracted out, is not green but instead in RANGE B, 1100-1700 nanometers. The skin structure is significantly suppressed in RANGE B where it is clearly visible in the visible light image.

Figure 3A:
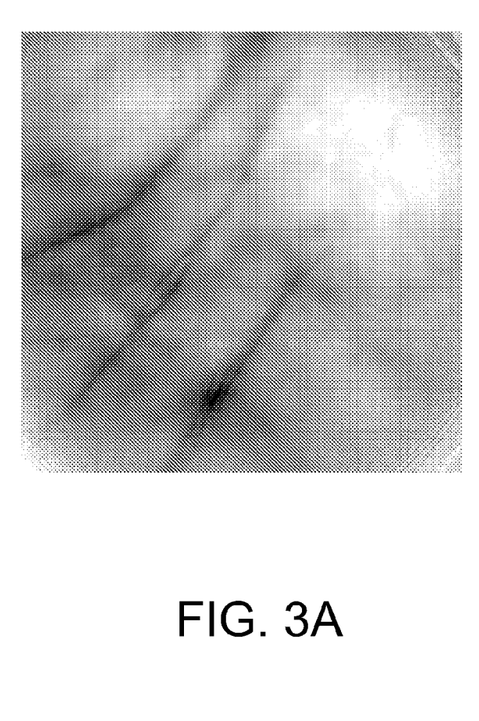
FIG. 3A depicts the left palm of a 62-year-old male imaged at 600-700 nm, circularly polarized.
Figure 3B:
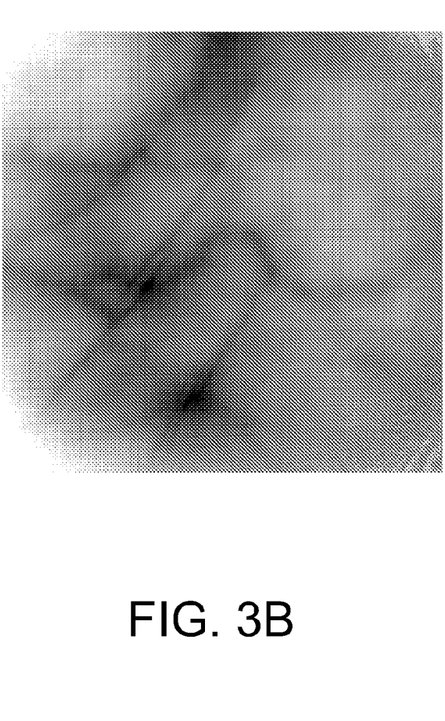
FIG. 3B depicts the left palm of the 62-year-old male of FIG. 3A imaged at 900-1000 nm, circularly polarized.
Figure 3C:
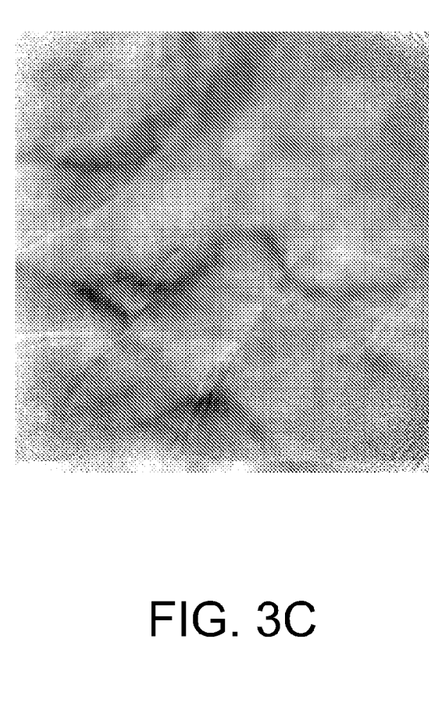
FIG. 3C depicts the weighted difference image between FIG. 3A and FIG. 3B.
Figure 4A:
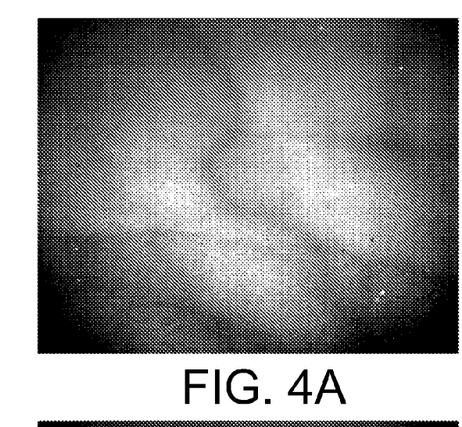
FIG. 4A depicts the unprocessed image of the left palm of a 62-year-old male, acquired using the FLIR ALPHA focal plane array camera at 950 nm.
Figure 4B:
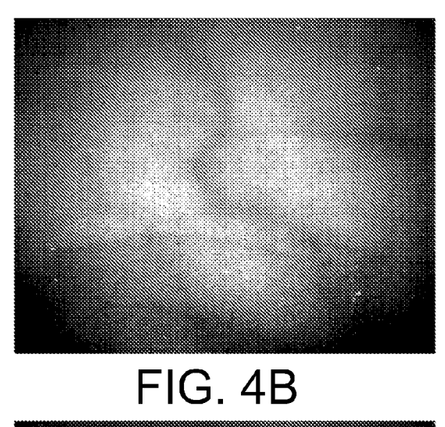
FIG. 4B depicts the unprocessed image of the left palm of the 62-year-old male of FIG. 4A, acquired using the FLIR ALPHA focal plane array camera at 1,000 nm.
Figure 4C:
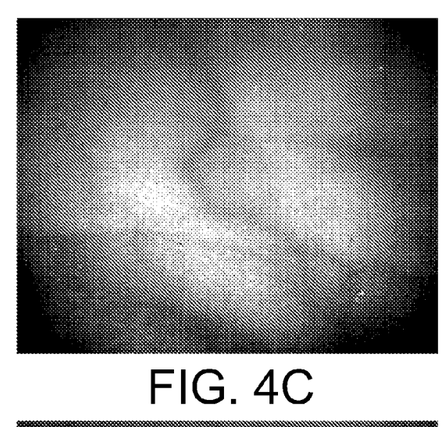
FIG. 4C depicts the unprocessed image of the left palm of the 62-year-old male of FIG. 4A, acquired using the FLIR ALPHA focal plane array camera at 1,050 nm.
Figure 4D:
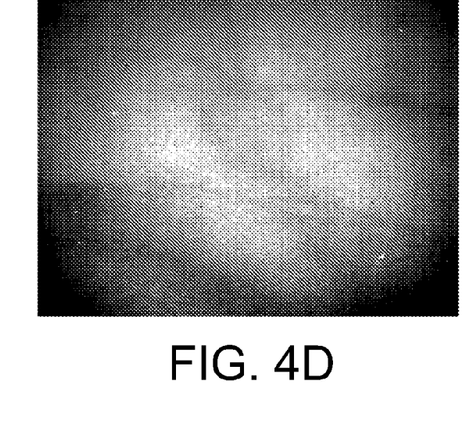
FIG. 4D depicts the unprocessed image of the left palm of the 62-year-old male of FIG. 4A, acquired using the FLIR ALPHA focal plane array camera at 1,100 nm.
Figure 4E:
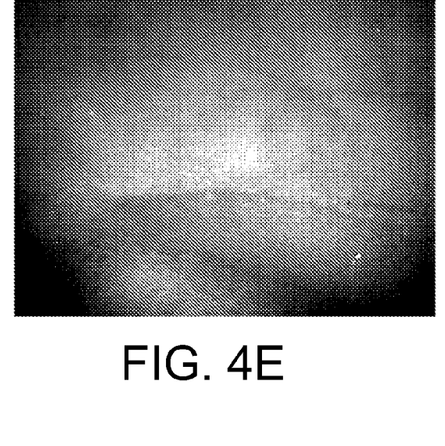
FIG. 4E depicts the unprocessed image of the left palm of the 62-year-old male of FIG. 4A, acquired using the FLIR ALPHA focal plane array camera at 1,150 nm.
Figure 4F:
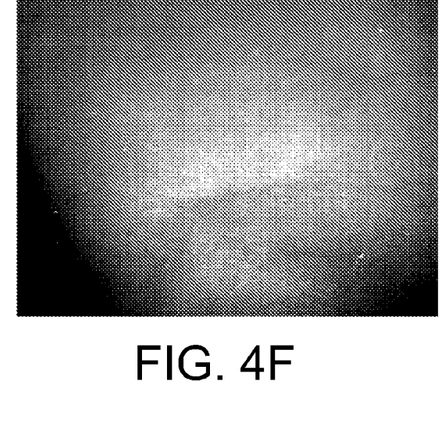
FIG. 4F depicts the unprocessed image of the left palm of the 62-year-old male of FIG. 4A, acquired using the FLIR ALPHA focal plane array camera at 1,200 nm.

Now referring FIGS. 3A-3C show the left palm of a 62 year old male imaged at 600-700 nanometers in FIG. 3A, 900-1000 nanometers in FIG. 3B and the weighted difference of those two images in FIG. 3C. The images in FIG. 3A and FIG. 3B are circularly polarized. This technique again shows how the weighted difference of the images can remove palm creases from the image, therefore making the image a clearer image of just the vasculature.

FIGS. 4A-4F show the unprocessed images of the left palm of a 62 year old male acquired using the FLIR ALPHA focal plane array camera which is an Indium Gallium Arsenide focal plane array camera at various infrared light wavelengths. Those wavelengths are 950 nanometers for FIG. 4A, 1000 nanometers for FIG. 4B, 1050 nanometers for FIG. 4C, 1100 nanometers for FIG. 4D, 1150 nanometers for FIG. 4E and 1200 nanometers for FIG. 4F. The images at FIGS. 4A, 4B and 4C all show veins clearly; however, the veins start to disappear at 1100 nanometers in FIG. 4D and are no longer visible by 1200 nanometers in FIG. 4F; however, all the other structures of the palm remain the same. This demonstrates why, image subtraction or division can enhance vein clarity while removing extraneous structures. When one image including veins and palm structure while another image has just the palm structure, those images may be compared to create an image of only the veins.

Figure 5A:
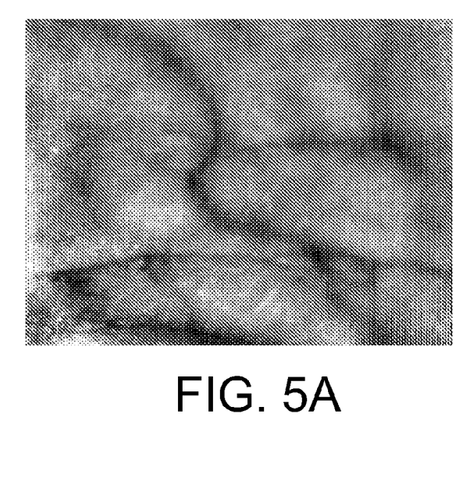
FIG. 5A depicts an image of the left palm of a 62-year-old male acquired using the FLIR ALPHA focal plane array camera at 1,000 nm with cross-polarized flat fielded.
Figure 5B:
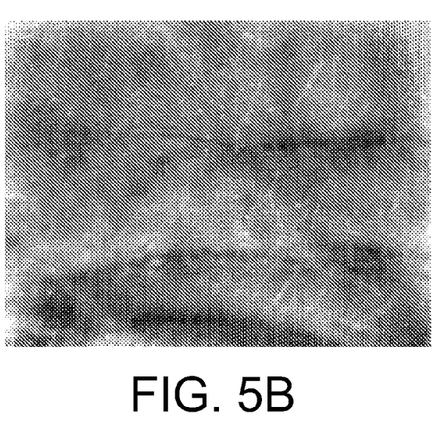
FIG. 5B depicts an image of the left palm of the 62-year-old male of FIG. 5A acquired using the FLIR ALPHA focal plane array camera at 1,300 nm with cross-polarized flat fielded.
Figure 5C:
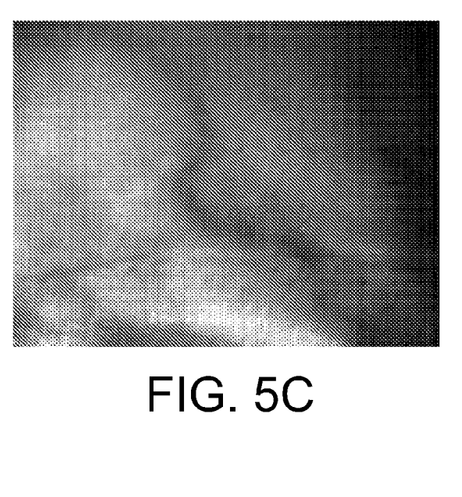
FIG. 5C depicts the ratio image of FIG. 5A and FIG. 5B.
Figure 5D:
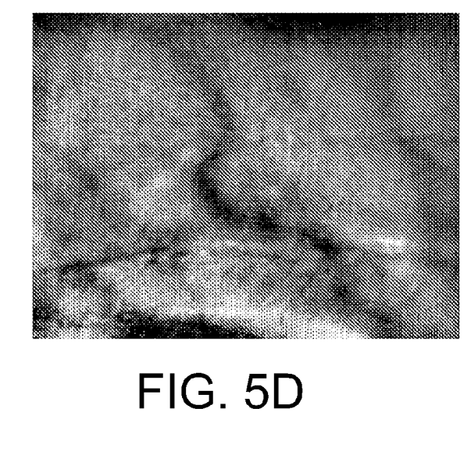
FIG. 5D depicts the ratio image FIG. 5C enhanced with large kernel and sharp masking.

Now referring to FIG. 5A-5D, these images are again of the left palm of the 62 year old male acquired using the FLIR ALPHA focal plane array camera which is an Indium Gallium Arsenide focal plane array camera. FIG. 5A is the image at 1000 nanometers with crossed polarizers and flat fielded. FIG. 5B is the image at 1300 nanometers with crossed polarizers and flat fielded. FIG. 5C is the ratio of the images in FIG. 5A and FIG. 5B. The veins are visible in FIG. 5A while not visible in FIG. 5B while the palm structure remains in both images. The ratio image in FIG. 5C is not completely clear because the palm shifted slightly from FIG. 5A to FIG. 5B; therefore creating some difficulty when the ratio took place because the palm structure did not overlap completely. In the preferred embodiment of the invention, this difficulty is overcome by the simultaneous recording of the two images to be compared by either weighted difference, ratio, or ratio after constants are added such that the position of the region to be imaged does not change from one image to the other. FIG. 5D shows the ratio image of FIG. 5C with large kernel unsharp masking, as that method of image processing is disclosed in U.S. Pat. No. 5,969,754. FIG. 5D adjusts for brightness variation and shows that the upper crease of the palm shown in FIG. 5A and FIG. 5B was removed by the ratio image and the lower crease was also removed to some extent, thus, even though the subject moved slightly between the two images, the ratio image still created a clearer image than the image without comparison of two images in RANGE A and RANGE B.

Figure 6A:
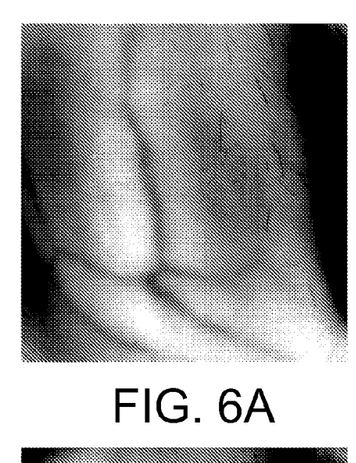
FIG. 6A depicts the flat fielded image of the left wrist of a 42-year-old male acquired using the PIXIS COOLED CCD t.v. camera at 800 nm.
Figure 6B:
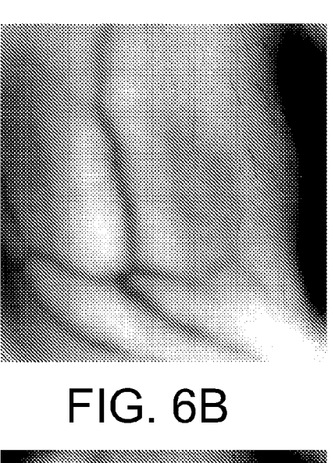
FIG. 6B depicts the flat fielded image of the left wrist of the 42-year-old male of FIG. 6A acquired using the PIXIS COOLED CCD t.v. camera at 900 nm.
Figure 6C:
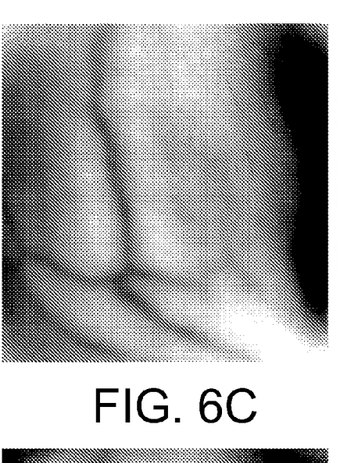
FIG. 6C depicts the flat fielded image of the left wrist of the 42-year-old male of FIG. 6A acquired using the PIXIS COOLED CCD t.v. camera at 1,000 nm.
Figure 6D:
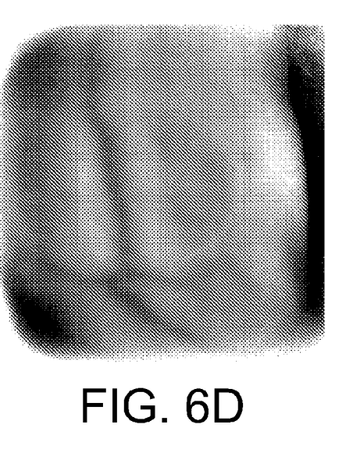
FIG. 6D depicts the flat fielded image of the left wrist of the 42-year-old male of FIG. 6A acquired using the PIXIS COOLED CCD t.v. camera at 1,100 nm.
Figure 6E:
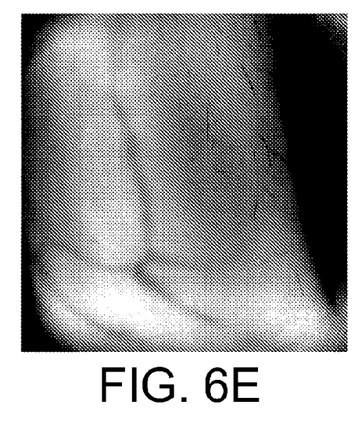
FIG. 6E depicts the ratio of the images at FIG. 6A and FIG. 6D.
Figure 6F:
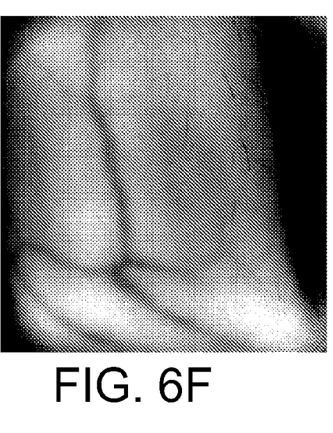
FIG. 6F depicts the ratio of the images at FIG. 6B and FIG. 6D.
Figure 6G:
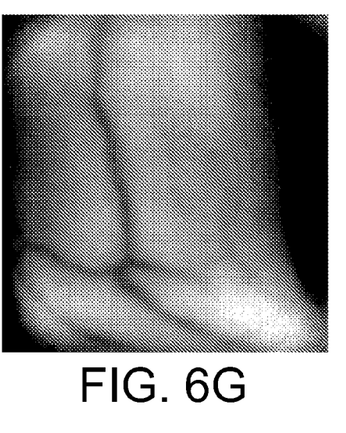
FIG. 6G depicts the ratio of the images at FIG. 6C and FIG. 6D.

Now referring to the images at FIGS. 6A-6G, these images are the flat fielded images of the left wrist of a 42 year old male acquired using the Pixis-cooled CCD tv camera at 800 nanometers in FIG. 6A, 900 nanometers in FIG. 6B, 1000 nanometers in FIG. 6C and 1100 nanometers in FIG. 6D. The FIGS. 6E, 6F and 6G are ratio images; FIG. 6E is the ratio of FIG. 6A and FIG. 6D, FIG. 6F is the ratio image of FIG. 6B and FIG. 6D, and FIG. 6G is the ratio image of FIG. 6C and FIG. 6D. While the tendons on either side of the central vertical vein are fairly apparent in FIG. 6A-FIG. 6D as the white features on either side of the central vertical vein, they are significantly repressed in the ratio images, FIG. 6E-FIG. 6G. This is another indication that the comparison of the two images is significant to remove non-vasculature structure, therefore providing a clearer image of just the vasculature to be reproduced onto the skin by the video projector.

Figure 7A:
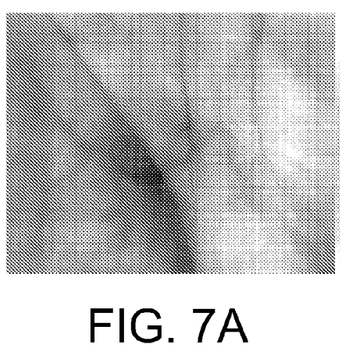
FIG. 7A depicts the unprocessed image of the right palm of a 43-year-old male, acquired using the FLIR ALPHA focal plane array camera at 1,000 nm.
Figure 7B:
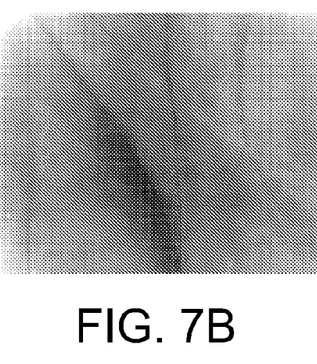
FIG. 7B depicts the unprocessed image of the right palm of the 43-year-old male of FIG. 7A, acquired using the FLIR ALPHA focal plane array camera at 1,200 nm.
Figure 7C:
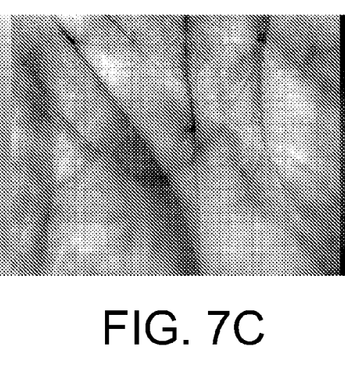
FIG. 7C depicts the image of FIG. 7A with edge enhancement.
Figure 7D:
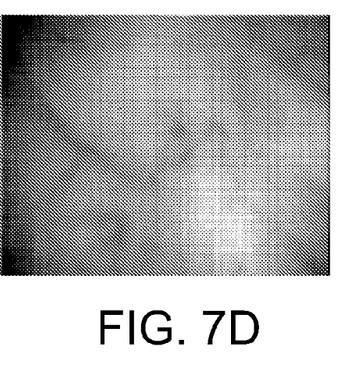
FIG. 7D depicts the ratio of the image at FIG. 7A and the image at FIG. 7B, after a constant has been added to the image at FIG. 7B.
Figure 7E:
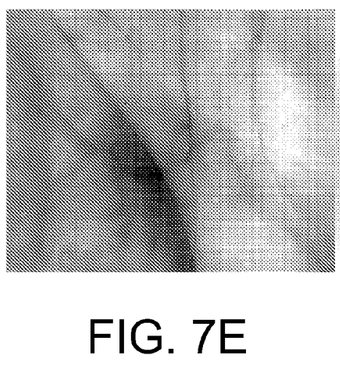
FIG. 7E depicts the unprocessed image of the right palm of the 43-year-old male of FIG. 7A, acquired using the FLIR ALPHA focal plane array camera at 1,000 nm.
Figure 7F:
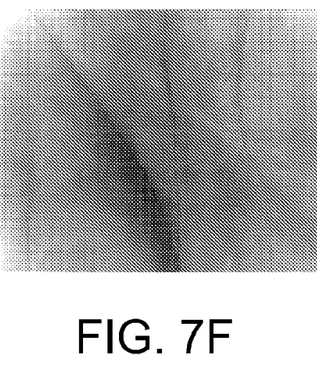
FIG. 7F depicts the unprocessed image of the right palm of the 43-year-old male of FIG. 7A, acquired using the FLIR ALPHA focal plane array camera at 1,200 nm.
Figure 7G:
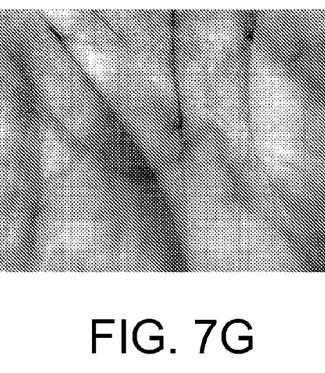
FIG. 7G depicts the image of FIG. 7E with edge enhancement.
Figure 7H:
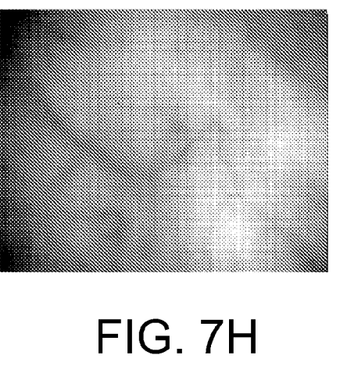
FIG. 7H depicts the image generated by taking the ratio of the image at FIG. 7E and the image at FIG. 7F after a constant has been added to the image at FIG. 7F.

FIGS. 7A-7H show image combination experiments using the FLIR Alpha camera on the palm of the right hand of a 43-year-old male. The camera was used in video capture mode with a filter wheel in front of the lens rotated to select 1000 nanometers and 1200 nanometers band pass filters alternatively. In this experiment, 500 frames were captured at 30 frames per second and two images were acquired at each wavelength. FIGS. 7A and 7E are the images acquired at 1000 nanometers. FIGS. 7B and 7F are the images acquired at 1200 nanometers. It can be observed in these images that the vascular structure is apparent in the images acquired at 1000 nanometers, FIGS. 7A and 7E; however the vasculature becomes less apparent or invisible at the higher wavelength 1200 nanometers in FIGS. 7B and 7F. The skin structure and palm creases are visible in both sets of images. FIGS. 7C and 7G show the edge-enhanced 1000 nanometer images. FIG. 7C is the edge-enhanced version of FIG. 7A and FIG. 7G is the edge-enhanced version of FIG. 7E. While the edge enhancement increases the visibility of the underlying vasculature, it also increases the prominence of the skin structure and palm creases therefore making the vasculature still hard to discern from other elements of the images despite the edge enhancement. FIGS. 7D and 7H were generated using the formula $(A+I_1)/(B+I_2)$ where A and B were constants, $I_1$ was the image at 1000 nanometers, and $I_2$ was the image at 1200 nanometers. The image of FIG. 7D was generated using the formula where A was zero, B was a nonzero constant, $I_1$ was the image at FIG. 7A, and $I_2$ was the image at FIG. 7B. The image of FIG. 7H was generated using the formula where A was zero, B was a nonzero constant, $I_1$ was the image at FIG. 7E, and $I_2$ was the image at FIG. 7F. Both FIG. 7D and FIG. 7H show that the vasculature is significantly more visible in the compared image because the skin structure and palm creases are removed by the comparison leaving only the vasculature.

Figure 8A:
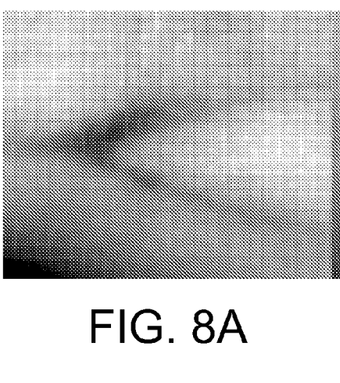
FIG. 8A depicts the unprocessed image of the left antecubital vein area of a 62-year-old male, acquired using the FLIR ALPHA focal plane array camera at 1,000 nm.
Figure 8B:
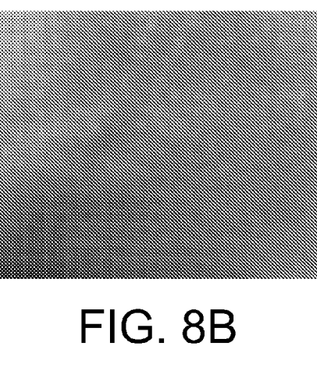
FIG. 8B depicts the unprocessed image of the left antecubital vein area of the 62-year-old male of FIG. 8A, acquired using the FLIR ALPHA focal plane array camera at 1,200 nm.
Figure 8C:
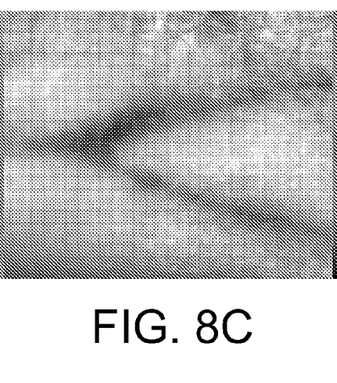
FIG. 8C depicts the image of FIG. 8A with edge enhancement.
Figure 8D:
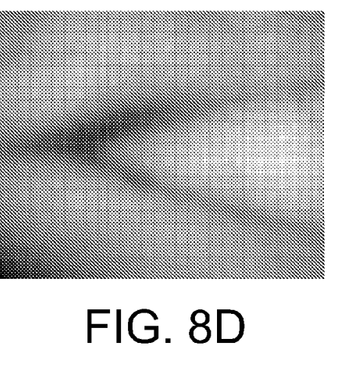
FIG. 8D depicts the image generated by taking the ratio of the image at FIG. 8A and the image at FIG. 8B after a constant has been added to the image at FIG. 8B.
Figure 8E:
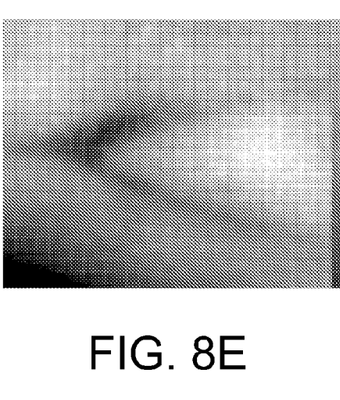
FIG. 8E depicts the unprocessed image of the left antecubital vein area of the 62-year-old male of FIG. 8A, acquired using the FLIR ALPHA focal plane array camera at 1,000 nm.
Figure 8F:
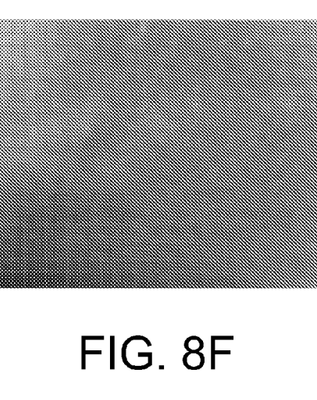
FIG. 8F depicts the unprocessed image of the left antecubital vein area of the 62-year-old male of FIG. 8A, acquired using the FLIR ALPHA focal plane array camera at 1,200 nm.
Figure 8G:
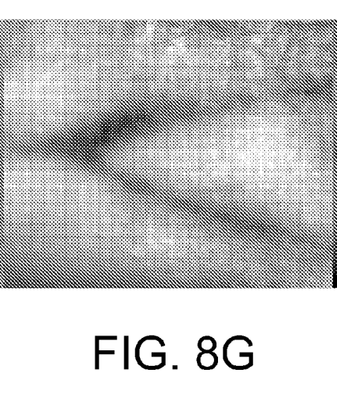
FIG. 8G depicts the image of FIG. 8E with edge enhancement.
Figure 8H:
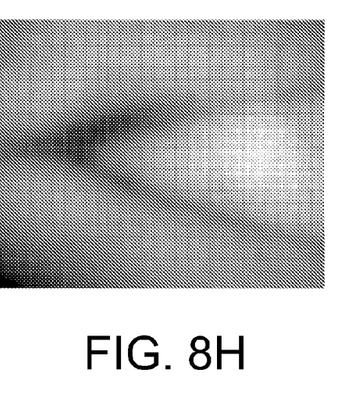
FIG. 8H depicts the image generated by taking the ratio of the image at FIG. 8E and the image of FIG. 8F after a constant has been added to the image at FIG. 8F.

FIGS. 8A-8H show image combination experiments using the FLIR Alpha camera on the left antecubital vein area of a 62-year-old male. The camera was used in video capture mode and a filter wheel in front of the lens was rotated to select 1000 nanometer and 1200 nanometer band pass filters alternatively. In this experiment, 500 frames were captured at 30 frames per second and 2 images were required at each wavelength. FIGS. 8A and 8E are images acquired at 1000 nanometers, FIGS. 8B and 8F are images acquired at 1200 nanometers. It is again apparent from these images that the vasculature is readily apparent at 1000 nanometers but nearly disappears at 1200 nanometers. The skin structure is visible in both the 1000 nanometers and 1200 nanometer images. FIGS. 8C and 8G are the edge-enhanced versions of FIGS. 8A and 8E respectively. These show that while the visibility of the vasculature can be increased by edge enhancement, edge enhancement also increases the prominence of skin structure. FIG. 8D was generated using the formula $(A+I_1)/(B+I_2)$ where A was zero, B was a constant, $I_1$ was the image at FIG. 8A, and $I_2$ was the image at FIG. 8B. This image shows that while the skin structure is removed by the comparison, the vasculature becomes more apparent due to the lack of other structures obscuring the view. FIG. 8H was generated using the formula $(A+I_1)/(B+I_2)$ where A was zero, B was a constant, $I_1$ was the image at FIG. 8E, and $I_2$ was the image at FIG. 8F. This again shows the increased vascular visibility with decreased skin structure obscuring the generated image.

Figure 9A:
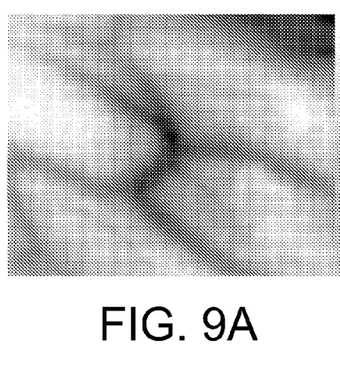
FIG. 9A depicts the unprocessed image of the back of the left hand of a 62-year-old male, acquired using the FLIR ALPHA focal plane array camera at 1,000 nm.
Figure 9B:
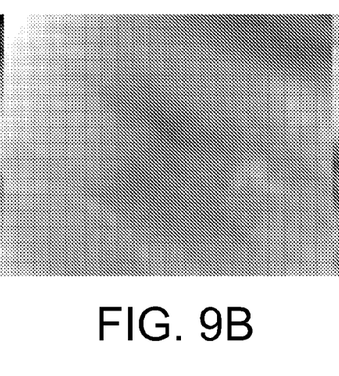
FIG. 9B depicts the unprocessed image of the back of the left hand of the 62-year-old male of FIG. 9A, acquired using the FLIR ALPHA focal plane array camera at 1,200 nm.
Figure 9C:
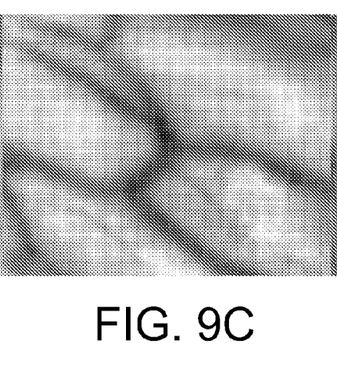
FIG. 9C depicts the image of FIG. 9A with edge enhancement.
Figure 9D:
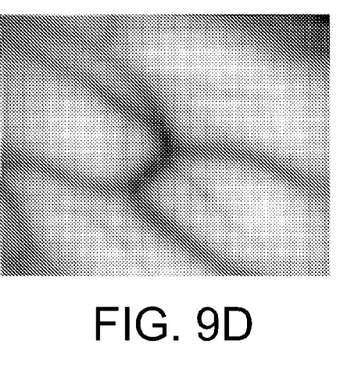
FIG. 9D depicts the image generated by taking the ratio of the image at FIG. 9A and the image at FIG. 9B after a constant has been added to the image at FIG. 9B.
Figure 9E:
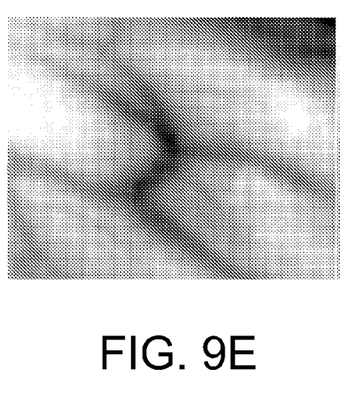
FIG. 9E depicts the unprocessed image of the back of the left hand of the 62-year-old male of FIG. 9A acquired using the FLIR ALPHA focal plane array camera at 1,000 nm.
Figure 9F:
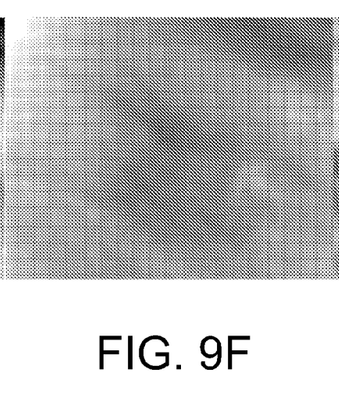
FIG. 9F depicts the unprocessed image of the back of the left hand of the 62-year-old male of FIG. 9A acquired using the FLIR ALPHA focal plane array camera at 1,200 nm.
Figure 9G:
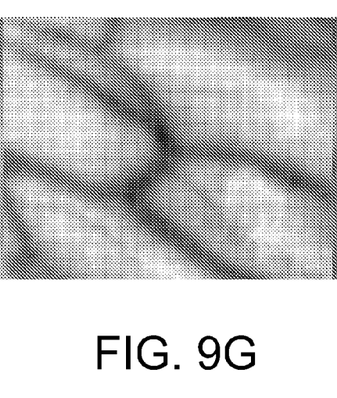
FIG. 9G depicts the image of FIG. 9E with edge enhancement.
Figure 9H:
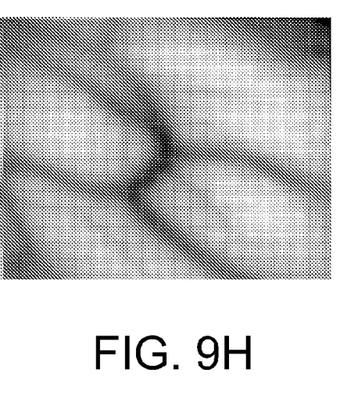
FIG. 9H depicts the image generated by taking the ratio of the image at FIG. 9E and the image at FIG. 9F after a constant has been added to the image at FIG. 9F.

FIGS. 9A-9H show image combination experiments using the FLIR Alpha camera on the back of the left hand of a 62-year-old male. The Alpha camera was used in video capture mode and a filter wheel in front of the lens was rotated to select 1000 nanometer and 1200 nanometer band pass filters alternatively. In this experiment, 500 frames were captured at 30 frames per second and 2 images were required at each wavelength. FIGS. 9A and 9E are images acquired at 1000 nanometers. FIGS. 9B and 9F are images acquired at 1200 nanometers. FIGS. 9C and 9G are the edge-enhanced versions of the image at FIG. 9A and the image at FIG. 9E respectively. These images yet again show that edge enhancement, while increasing the visibility of underlying vasculature, also increase the visibility of skin structure which can preclude the discernability of the underlying vasculature as opposed to other structures which are recorded by the camera. The image at FIG. 9D was generated using the formula $(A+I_1)/(B+I_2)$ where A was zero, B was a constant, $I_1$ was the image at FIG. 9A, and $I_2$ was the image at FIG. 9B. The underlying vasculature is made more clear by subtracting out the overlying skin structure thereby leaving solely the vasculature. The image at FIG. 9H was generated using the formula $(A+I_1)/(B+I_2)$ where A was zero, B was a constant, $I_1$ was the image at FIG. 9E, and $I_2$ was the image at FIG. 9F. This repeats the results of the image at FIG. 9D and shows that the results are consistent when the experiment is repeated.

Figure 10A:
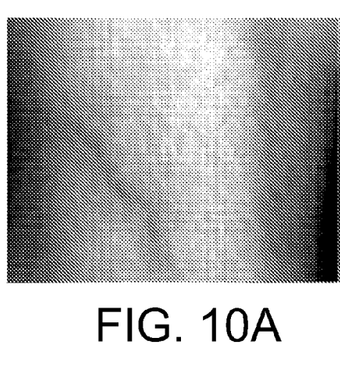
FIG. 10A depicts the unprocessed image of the side of the left leg of a 24-year-old female acquired using the FLIR ALPHA focal plane array camera at 1,000 nm.
Figure 10B:
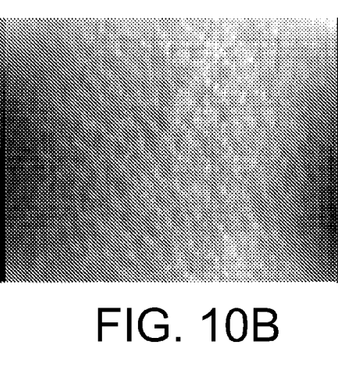
FIG. 10B depicts the unprocessed image of the side of the left leg of the 24-year-old female of FIG. 10A acquired using the FLIR ALPHA focal plane array camera at 1,200 nm.
Figure 10C:
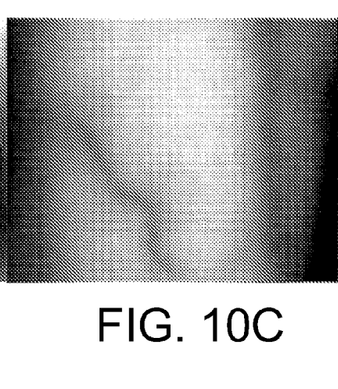
FIG. 10C depicts the image generated by taking the ratio of the image at FIG. 10A and the image at FIG. 10B after a constant has been added to the image at FIG. 10B.
Figure 10D:
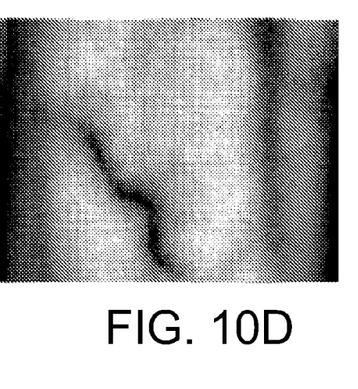
FIG. 10D depicts the image at FIG. 10C with edge enhancement.
Figure 10E:
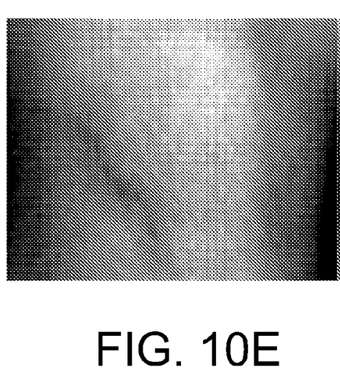
FIG. 10E depicts the unprocessed image of the side of the left leg of the 24-year-old female of FIG. 10A acquired using the FLIR ALPHA focal plane array camera at 1,000 nm.
Figure 10F:
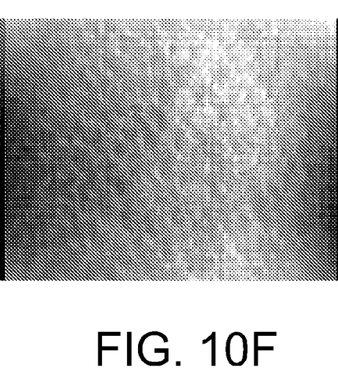
FIG. 10F depicts the unprocessed image of the side of the left leg of the 24-year-old female of FIG. 10A acquired using the FLIR ALPHA focal plane array camera at 1,200 nm.
Figure 10G:
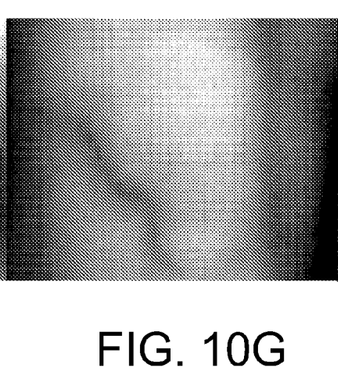
FIG. 10G depicts the image generated by taking the ratio of the image at FIG. 10E and the image at FIG. 10F after a constant has been added to the image at FIG. 10F.
Figure 10H:
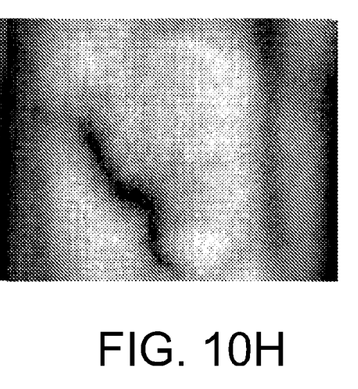
FIG. 10H depicts the image at FIG. 10G with edge enhancement.

FIGS. 10A-10H show image combination experiments using the FLIR Alpha camera on the side of the left leg of a 24-year-old female. The Alpha camera was used in video capture mode and a filter wheel in front of the lens was rotated to select 1000 nanometer and 1200 nanometer band pass filters alternatively. In this experiment, 500 frames were captured at 30 frames per second and 2 images were required at each wavelength. FIGS. 10A and 10E show images acquired at 1000 nanometers. FIGS. 10B and 10F show images acquired at 1200 nanometers. The image at FIG. 10C was generated using the formula $(A+I_1)/(B+I_2)$ where A was zero, B was a constant, $I_1$ was the image at FIG. 10A, and $I_2$ was the image at FIG. 10B. The image at FIG. 10G was generated using the formula $(A+I_1)/(B+I_2)$ where A was zero, B was a constant, $I_1$ was the image at FIG. 10E, and $I_2$ was the image at FIG. 10F. Both FIG. 10C and FIG. 10G show that while skin structure is clearly visible in FIG. 10A and FIG. 10B, this comparison process removes the skin structure from the image leaving solely the vasculature, making the vasculature much more prominent and easily seen. FIG. 10D is the edge-enhanced version of FIG. 10C, and FIG. 10H is the edge-enhanced version of FIG. 10G. These images show that while edge enhancement before the skin structure is removed does not help to remove skin structure, thereby only being of limited use, edge enhancement after the comparison of the images can further increase the prominence of underlying vasculature making the location of the vasculature from these images significantly improved.

The data evidenced by FIGS. 2A-10H make it evident that the quality of the imaging of the vasculature probably peaks between 900 nanometers and 1000 nanometers, thus making an ideal range for imaging the vasculature 900-1000 nanometers and it also makes it apparent that the comparing of two images one containing a good image of the vasculature but also containing other features of the object being imaged, and the other one containing an image with no vasculature features but showing the other features of the object being imaged such as tendons and skin structure can significantly improve the quality of the image to be reprojected on the skin by removing much of the non-vasculature structures therefore making the vasculature in the reprojected image more clear.

Although the present invention has been described and illustrated with respect to a preferred embodiment and a preferred use therefor, it is not to be so limited since modifications and changes can be made therein which are within the full intended scope of the invention.

What is claimed is:

1. An apparatus to enhance the visibility of buried structure beneath a surface of an object, the apparatus comprising:
   at least one illumination source for illuminating the buried structure with infrared light in a first range at which subcutaneous blood vessels are visible and in a second range at which subcutaneous blood vessels are less visible;

a first imaging device configured to receive infrared light in the first range reflected from the object and configured to produce a first image;

a second imaging device configured to receive infrared light in the second range reflected from the object and configured to produce a second image;

an image processor configured to compare the first image and the second image to generate a compared image;

a video projector configured to project said compared image onto the surface of the object wherein the received infrared light in the first range and infrared light in the second range reflected from the object are coaxial with the projected compared image, and a filter, wherein said filter prevents said compared image from reaching said first imaging device or said second imaging device.

2. The apparatus of claim 1 further comprising:

a first polarizing filter configured to polarize the infrared light from the at least one illumination source before the infrared light is reflected from the object.

3. The apparatus of claim 2 further comprising:

a second polarizing filter, oriented perpendicular to the first polarizing filter, configured to polarize the infrared light in the first range reflected from the object and the infrared light in the second range reflected from the object.

4. A method for imaging body tissue to enhance the visibility of a subcutaneous blood vessel beneath a surface of the body tissue comprising:

providing the apparatus of claim 1;

illuminating a subcutaneous blood vessel with infrared light;

receiving infrared light reflected from the body tissue;

projecting a visible light image of the subcutaneous blood vessel based on the received infrared light onto the surface of the body tissue coaxially with the received infrared light reflected from the body tissue, and filtering light reflected from the body tissue to prevent said visible light image to be recorded by the first imaging device or the second imaging device of said apparatus of claim 1.

5. An apparatus to enhance the visibility of buried structure beneath a surface of an object, the apparatus comprising:

an illumination source configured to illuminate the buried structure with infrared light in the range of 1000 to 1100 nanometers;

an imaging device configured to receive infrared light in the range of 1000 to 1100 nanometers reflected from the object and configured to produce a first image;

a video projector configured to project a visible light image of the buried structure based on the first image onto the surface of the object, wherein the received infrared light reflected from the object is coaxial with the projected visible light image; and a filter, wherein said filter prevents said visible light image from reaching said imaging device when reflected from said object.

6. A method for imaging body tissue to enhance the visibility of a subcutaneous blood vessel beneath a surface of the body tissue comprising:

providing the apparatus of claim 5;

illuminating a subcutaneous blood vessel with infrared light;

receiving infrared light reflected from the body tissue; and projecting a visible light image of the subcutaneous blood vessel based on the received infrared light onto the surface of the body tissue; wherein the projected visible light image is coaxial with the received infrared light reflected from the body tissue, and filtering light reflected from the body tissue to prevent said visible light image to be recorded by the imaging device of said apparatus of claim 5.

* * * * *